United States Patent
Liu et al.

(10) Patent No.: US 8,716,504 B2
(45) Date of Patent: May 6, 2014

(54) EPOXIDATION PROCESSES

(71) Applicant: Dow Technology Investments, LLC, Midland, MI (US)

(72) Inventors: Albert C. Liu, Charleston, WV (US); Hwaili Soo, Charleston, WV (US)

(73) Assignee: Dow Technology Investments LLC, Midland, MI (US)

(*) Notice: Subject to any disclaimer, the term of this patent is extended or adjusted under 35 U.S.C. 154(b) by 0 days.

(21) Appl. No.: 14/020,528

(22) Filed: Sep. 6, 2013

(65) Prior Publication Data

US 2014/0012019 A1 Jan. 9, 2014

Related U.S. Application Data

(62) Division of application No. 12/760,044, filed on Apr. 14, 2010, now Pat. No. 8,546,294.

(60) Provisional application No. 61/171,209, filed on Apr. 21, 2009.

(51) Int. Cl.
C07D 301/10 (2006.01)
C07D 301/03 (2006.01)
B01J 23/00 (2006.01)
B01J 21/00 (2006.01)

(52) U.S. Cl.
USPC ............ 549/534; 549/536; 502/241; 502/250; 502/254; 502/255; 502/355; 502/415; 502/439

(58) Field of Classification Search
USPC .......... 549/534, 536; 502/241, 250, 254, 255, 502/355, 415, 439
See application file for complete search history.

(56) References Cited

U.S. PATENT DOCUMENTS

| | | | |
|---|---|---|---|
| 4,829,043 A | 5/1989 | Boehning et al. |
| 4,908,343 A | 3/1990 | Bhasin |
| 5,057,481 A | 10/1991 | Bhasin |
| 5,081,096 A | 1/1992 | Monnier et al. |
| 5,102,848 A | 4/1992 | Soo et al. |
| 5,187,140 A | 2/1993 | Thorsteinson et al. |
| 5,380,697 A | 1/1995 | Buffum et al. |
| 5,418,202 A | 5/1995 | Evans et al. |
| 5,504,053 A | 4/1996 | Chou et al. |
| 5,597,773 A | 1/1997 | Evans et al. |
| 5,703,253 A | 12/1997 | Evans et al. |

(Continued)

FOREIGN PATENT DOCUMENTS

| | | |
|---|---|---|
| WO | 2005023417 A1 | 3/2005 |
| WO | 2005023418 A1 | 3/2005 |

(Continued)

OTHER PUBLICATIONS

International Search Report and Written Opinion, PCT/US2009/042055, mailed Feb. 28, 2011.

*Primary Examiner* — Cam N. Nguyen
(74) *Attorney, Agent, or Firm* — Lois K. Ruszala; KSJLaw, LLC

(57) ABSTRACT

The present invention provides rhenium-promoted epoxidation catalysts based upon shaped porous bodies comprising a minimized percentage of their total pore volume being present in pores having diameters of less than one micron, and a surface area of at least about 1.0 $m^2/g$. Processes of making the catalysts and using them in epoxidation processes are also provided.

12 Claims, 9 Drawing Sheets

(56) References Cited

U.S. PATENT DOCUMENTS

| | | | |
|---|---|---|---|
| 5,801,259 A | 9/1998 | Kowaleski | |
| 5,929,259 A | 7/1999 | Lockemeyer | |
| 6,083,870 A | 7/2000 | Gaffney et al. | |
| 6,831,037 B2 | 12/2004 | Szymanski et al. | |
| 7,049,451 B2 | 5/2006 | Ehara et al. | |
| 7,307,844 B2 | 12/2007 | Wu | |
| 7,402,612 B2 | 7/2008 | Jin et al. | |
| 7,485,597 B2 | 2/2009 | Lockemeyer et al. | |
| 7,560,577 B2 | 7/2009 | Hirota et al. | |
| 7,825,062 B2 | 11/2010 | Gerdes et al. | |
| 7,910,518 B2 | 3/2011 | Pak et al. | |
| 7,932,408 B2 | 4/2011 | Gueckel | |
| 7,977,274 B2 | 7/2011 | Gueckel | |
| 8,084,390 B2 | 12/2011 | Gerdes et al. | |
| 8,084,632 B2 * | 12/2011 | Liu et al. | 549/523 |
| 2004/0049061 A1 | 3/2004 | Lockemeyer et al. | |
| 2004/0127586 A1 | 7/2004 | Espinoza et al. | |
| 2004/0198992 A1 | 10/2004 | Hess et al. | |
| 2005/0096219 A1 | 5/2005 | Gerdes et al. | |
| 2006/0258532 A1 | 11/2006 | Bhasin et al. | |
| 2006/0293180 A1 | 12/2006 | Thosteinson | |
| 2007/0037991 A1 | 2/2007 | Rizkalla | |
| 2007/0184973 A1 | 8/2007 | Gerdes et al. | |
| 2008/0081920 A1 | 4/2008 | Gueckel | |
| 2008/0306289 A1 | 12/2008 | Hess et al. | |
| 2009/0062556 A1 | 3/2009 | Pak | |
| 2009/0177000 A1 | 7/2009 | Bhasin et al. | |
| 2009/0227820 A1 | 9/2009 | Pak et al. | |
| 2009/0270249 A1 | 10/2009 | Bauer et al. | |
| 2009/0275763 A1 | 11/2009 | Serafin et al. | |
| 2010/0056816 A1 | 3/2010 | Wallin et al. | |
| 2010/0179336 A1 | 7/2010 | Pak | |
| 2010/0191006 A1 | 7/2010 | Guckel | |
| 2012/0189833 A1 | 7/2012 | Garces et al. | |

FOREIGN PATENT DOCUMENTS

| | | |
|---|---|---|
| WO | 2005039757 A1 | 5/2005 |
| WO | 2006028940 A1 | 3/2006 |
| WO | 2006133183 A1 | 12/2006 |
| WO | 2006133187 A1 | 12/2006 |
| WO | 2007085206 A1 | 8/2007 |
| WO | 2007123932 A2 | 11/2007 |
| WO | 2008054564 A1 | 5/2008 |

* cited by examiner

Cumulative Intrusion vs Pore size

EPOXIDATION PROCESSES

CROSS REFERENCE TO RELATED APPLICATIONS

This is a divisional application of U.S. patent application Ser. No. 12/760,044, filed Apr. 14, 2010, now U.S. Pat. No. 8,546,294, which claims the benefit of U.S. provisional patent application Ser. No. 61/171,209, filed Apr. 21, 2009.

FIELD OF THE INVENTION

Provided herein are rhenium-promoted epoxidation catalysts as well as methods for making the catalysts and for their use in the production of other end-use products.

BACKGROUND

Many facets of the practice of chemistry and/or chemical engineering can be reliant upon providing structures or surfaces capable of performing or facilitating separations or reactions and/or providing areas for such separations or reactions to take place. Such structures or surfaces are thus ubiquitous in many R&D and manufacturing settings. Although the desired physical and chemical properties of these shaped bodies can, and will, vary depending on the particular application, there are certain properties that are generally desirable in such shaped bodies regardless of the final application in which they will be utilized.

For example, such shaped bodies will desirably be of high purity and substantially inert so that the shaped bodies themselves will not participate in the separations or reactions taking place around, on or through them in a way that is undesired, unintended, or detrimental. For those shaped bodies for which it is desired to have the components being reacted or separated pass through, or diffuse into, the shaped body, a low diffusion resistance would be advantageous. For those shaped bodies desirably utilized as reaction surfaces or catalyst supports, high surface area can be desired, to improve the loading and dispersion of the desired reactants and/or catalytic species, and also to provide enhanced surface area on which the reactions or separations can take place.

Oftentimes, the desired properties of such shaped bodies can conflict with one another, and as a result, preparing shaped bodies where each desired property is maximized can be challenging. In efforts to meet these challenges, much research has been conducted not only on the components and additives utilized in the bodies, but also on the physical properties of shaped bodies so formed. However, many of the shaped porous bodies developed to date have yet to provide the full spectrum of desired properties for these materials.

Desirably, shaped porous bodies would be provided that could optimize a plurality of properties, or at least optimize at least one property without substantial detriment to another. Such shaped porous bodies would provide improvements to products, e.g., catalysts, in which they were used.

SUMMARY OF THE INVENTION

The present invention provides shaped porous bodies having an optimized pore size distribution as well as an enhanced surface area. More particularly, it has now been discovered that shaped porous bodies having a pore size distribution wherein the percentage of total pore volume present in pores having diameters less than one micron is minimized can be provided, and yet also exhibit surface areas of greater than 1.0 $m^2/g$. As such, diffusion resistance issues presented in conventional shaped porous bodies having a greater fraction of total pore volume in pores having diameters of less than one micron can substantially be avoided. The shaped porous bodies yet exhibit surface areas, e.g., 1.0 $m^2/g$, that provide the desired or required loading and dispersion of the desired reactants and/or catalytic species, and also provide enhanced surface area on which the reactions or separations can take place. These shaped porous bodies thus provide improved end-use products, such as catalysts, based upon them which in turn, can be employed in processes to produce additional end-use products downstream thereof.

In a first aspect, the present invention provides a rhenium-promoted epoxidation catalyst comprising at least one catalytic species and rhenium deposited on a shaped porous body. The shaped porous body desirably comprises a minimized percentage of total pore volume being present in pores having diameters of less than one micron, and a surface area of at least about 1.0 $m^2/g$. Desirably, the shaped porous body comprises a maximized percentage of total pore volume being present in pores having diameters of between about 1 micron and about 5 microns. The shaped porous body may desirably comprise alpha-alumina, which may further desirably be fluoride affected. The catalyst desirably comprises silver, and may comprise additional promoters in addition to rhenium, and in certain advantageous embodiments comprises rhenium and cesium.

Because the pore size distribution of the shaped porous body is optimized, i.e., with a minimized percentage of the total pore volume being present in pores having diameters smaller than 1 micron, the catalyst may exhibit reduced diffusion resistance, as may be shown by increased activity, or increased efficiency, or both increased activity and increased efficiency over catalysts based upon shaped porous bodies having a greater percentage of their total pore volume in pores having diameters of less than one micron. Surprisingly, the shaped porous bodies yet exhibit surface areas of greater than or equal to 1.0 $m^2/g$ so that the activity and/or efficiency of catalysts based upon the same is yet acceptable or enhanced over catalysts based upon shaped porous bodies having a greater percentage of their total pore volume in pores having diameters of less than one micron.

A process for making a catalyst is provided in a further aspect, the process comprising selecting a shaped porous body comprising a minimized percentage of the total pore volume being present in pores having diameters of less than one micron and a surface area of greater than or equal to about 1.0 $m^2/g$ and depositing at least one catalytic species on the shaped porous body.

The advantageous pore size distribution and surface area yet provided to the shaped porous bodies are expected to translate to improvements in one or more catalyst properties, which in turn, are expected to provide improvements to the processes in which the catalysts are utilized. As a result, and in yet another aspect, the present invention provides a process for the epoxidation of an alkylene. The process comprises reacting a feed comprising one or more alkylenes and oxygen in the presence of the catalyst based upon a shaped porous body comprising a minimized percentage of the total pore volume being present in pores having diameters of less than one micron and having a surface area of at least about 1.0 $m^2/g$. The catalysts of the present invention are expected to provide at least one enhanced property to the process, desirably without a concurrent substantial detriment to another.

The advantages provided to such processes can be further leveraged by utilization of the alkylene oxides produced thereby in further downstream processes, and such processes are thus provided in yet another aspect of the invention. More specifically, the present invention also provides a process for preparing a 1,2-diol, a 1,2-diol ether, a 1,2-carbonate, or an alkanolamine. The process comprises converting an alkylene oxide into the 1,2-diol, 1,2-diol ether, a 1,2-carbonate, or alkanolamine, wherein the alkylene oxide is prepared by a process utilizing a catalyst based upon a shaped porous body comprising a minimized percentage of its total pore volume being present in pores having diameters of less than one micron and a surface area of at least about 1.0 m$^2$/g.

DESCRIPTION OF THE DRAWINGS

These and other features, aspects and advantages of the present invention may be further understood and/or illustrated when the following detailed description is considered along with the attached drawings.

DETAILED DESCRIPTION OF THE INVENTION

Figure 1:
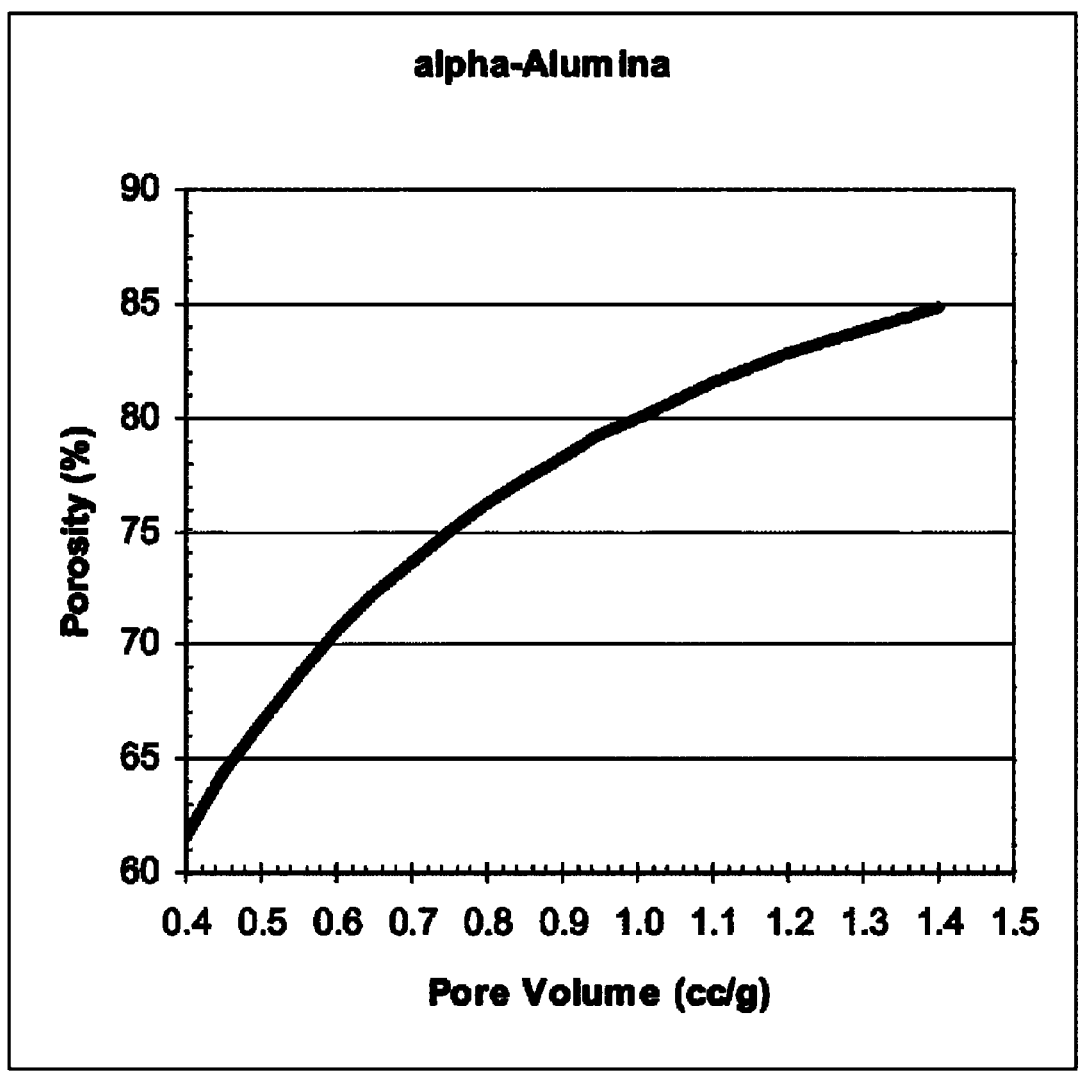
FIG. 1 is a graphical depiction of the relationship between porosity and pore volume.

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof; rather, and unless otherwise noted, terms are to be understood according to conventional usage by those of ordinary skill in the relevant art. Unless defined otherwise, technical and scientific terms used herein have the same meaning as is commonly understood by one of skill in the art to which this invention belongs.

The "selectivity" of an epoxidation reaction, which is synonymous with "efficiency," refers to the fraction, expressed as a percentage, of converted or reacted olefin that forms a particular product. The terms "efficiency" and "selectivity" are used interchangeably herein. The activity of an epoxidation reaction can be quantified in a number of ways, one being the mole percent of olefin oxide contained in an outlet stream of the reactor relative to that in an input stream (the mole percent of olefin oxide in the inlet stream typically, but not necessarily, approaches zero percent) while the reactor temperature is maintained substantially constant; and another being the temperature required to maintain a given rate of olefin oxide production. In many instances, activity is measured over a period of time in terms of the mole percent of olefin oxide produced at a specified constant temperature. Alternatively, activity can be measured as a function of the temperature required to sustain production of a specified constant mole percent of olefin oxide.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation. If ranges are disclosed, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.). The modifier "about" used in connection with a quantity is inclusive of the stated value and has the meaning dictated by the context (e.g., includes the degree of error associated with measurement of the particular quantity).

Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described inventive features may be combined in any suitable manner in the various embodiments.

The present invention provides catalysts based upon shaped porous bodies having optimized pore size distributions, desirably while yet maintaining surface areas comparable to commercially available shaped porous bodies useful in similar applications, e.g., as supports for catalysts. As used herein, the phrase, 'shaped porous body', is meant to indicate a solid which has been formed into a selected shape suitable for its intended use and that has been calcined or otherwise processed so as to have a porosity of greater than at least about 10%. In catalytic applications, the conventional belief has been that higher percentages of total pore volume being in pores having diameters of less than one micron provided optimal performance since these larger percentages of smaller pores provide a greater surface area on which reactions may take place.

However, it has now been surprisingly discovered that shaped porous bodies having a lower percentage of their total pore volume present in these smaller pores, e.g. less than 1 micron, can be used as the basis for catalysts that can, in turn, exhibit improved properties as compared to catalysts based upon shaped porous bodies comprising a pore size distribution wherein a higher percentage of the total pore volume resides in pores having diameters of less than 1 micron. While not wishing to be bound by any theory, it is thought that while a conventional pore size distribution may provide an enhanced surface area to the shaped porous bodies in which it is employed, it may also result in the presence of diffusional barriers that, in turn, can impair performance of a catalyst based upon such a shaped porous body.

Advantageously, the shaped porous bodies upon which the present catalysts are based comprise a minimized percentage of their total pore volume being present in pores having diameters of less than one micron. More particularly, less than about 25%, or less than 20%, or even less than 15%, of the total pore volume of the shaped porous bodies will desirably comprise pores having diameters of less than one micron. Rather, the percentage of the total pore volume being present as pores having diameters of between about 1 micron and about 5 microns will be maximized. In some embodiments, the percentage of the total pore volume present in pores having diameters of between about 1 micron and about 5 microns, will be at least about 75%, or about 80%, or even about 85% or greater. Even so, the shaped porous bodies, and thus catalysts based upon them, can exhibit surface areas of greater than or equal to about 1.0 $m^2/g$ or greater than about 1.15 $m^2/g$ or preferably greater than about 1.3 $m^2/g$.

"Surface area," as used herein, refers to the surface area of the shaped porous bodies as determined by the BET (Brunauer, Emmett and Teller) method by nitrogen as described in the Journal of the American Chemical Society 60 (1938) pp. 309-316. "Total pore volume" means pore volume of the shaped porous body and is typically determined by mercury porosimetry. The measurements reported herein used the method described in Webb & Orr, Analytical Methods in Fine Particle Technology (1997), p. 155, using mercury intrusion to 60,000 psia using Micromeritics Autopore IV 9520, assuming 130° contact angle, 0.485 N/M surface tension of Hg. "Porosity" is the proportion of the non-solid volume to the total volume of material. Total pore volume as measured by mercury porosimetry or water absorption may be used to estimate porosity by those of skill in the art. Put another way, porosity is defined as the void volume (unoccupied space) divided by the total volume of the sample. FIG. 1 shows the relationship between porosity and pore volume.

Void volume is the proportion of the non-solid volume to the mass of the material. It can be expressed as a fraction or a percentage. The void volume is measured directly by mercury porosimetry as the total pore volume (cc/g). The total volume of the sample is the void volume (i.e., the total pore volume) plus the volume taken up by the solid. For solid alpha-alumina the density is 4 g/cc, hence the volume taken up by the solid is 0.25 cc/g. Thus the porosity can be expressed as:

Porosity in percent=100%×(total pore volume in cc/g)/(0.25 cc/g+total pore volume in cc/g)

"Median pore diameter" means the pore diameter corresponding to the point in the pore size distribution at which half of the total pore volume of the shaped porous body has cumulatively been measured.

In certain embodiments, the shaped porous bodies will desirably be comprised largely of particles in the form of platelets having at least one substantially flat major surface having a lamellate or platelet morphology, at least 50 percent of which (by number) have a major dimension of less than about 50 microns. As used herein, the term "platelet" means that a particle has at least one substantially flat major surface, and that some of the particles have two, or sometimes more, flat surfaces. The "substantially flat major surface" referred to herein may be characterized by a radius of curvature of at least about twice the length of the major dimension of the surface.

As those of ordinary skill in the art are aware, shaped porous bodies may typically be comprised of many, typically thousands, tens of thousands, hundreds of thousands or even millions of smaller particles, and in the present application, it is the surface morphology or aspect ratio of these smaller particles that is observed or measured and referred to herein. As such, it is to be understood that when particular ranges are indicated as advantageous or desired for these measurements, or that a particular surface morphology has been observed, that these ranges may be based upon the measurement or observation of from about 1 to about 10 particles, and although it may generally be assumed that the majority of the particles may thus exhibit the observed morphology or be within the range of aspect ratio provided, that the ranges are not meant to, and do not, imply that 100% of the population, or 90%, or 80%, or 70%, or even 50% of the particles need to exhibit a surface morphology or possess an aspect ratio within this range.

The shaped porous bodies upon which the present catalysts are based may comprise any of the large number of porous refractory structure or support materials, so long as whatever the porous refractory material chosen, it is relatively inert in the presence of the chemicals and processing conditions employed in the application in which the shaped porous body will be utilized.

The shaped porous bodies may be prepared from precursor compositions comprising, for example, any of the transition alumina precursors, transition aluminas, hydrated aluminium compounds, alpha-alumina, silicon carbide, silicon dioxide, zirconia, zirconium silicate, graphite, magnesia and various clays. The use of transition alumina precursors, transition aluminas, or other alpha-alumina precursors, is preferred, as they may at least partially be converted to transition aluminas, or alpha-alumina, respectively, during processing. Mixtures of hydrated aluminum compounds, such as boehmite, gibbsite, or bayerite, or transition aluminas obtained by thermal dehydration of the hydrated aluminum compounds, may be suitable. Preferred alpha-alumina precursors in these embodiments of the invention comprise pseudo-boehmite, gibbsite, gamma-alumina and kappa-alumina.

As used herein, "transition alumina precursors" are one or more materials that, upon thermal treatment, are capable of being at least partially converted to transition alumina. Transition alumina precursors include, but are not limited to, aluminum tri-hydroxides, such as gibbsite, bayerite, and nordstrandite; and aluminum oxide hydroxides, such as boehmite, pseudo-boehmite and diaspore. "Transition aluminas" are one or more aluminas other than alpha-alumina, which are capable of being at least partially converted to alpha-alumina under thermal treatment at 900° C. or greater. Transition aluminas possess varying degrees of crystallinity, and include, but are not limited to gamma-alumina, delta-alumina, eta-alumina, kappa-alumina, chi-alumina, rho-alumina, and theta-alumina. "Alpha-alumina precursor" means one or more materials capable of being transformed into alpha-alumina, including transition alumina precursors and transition aluminas.

In certain embodiments, it can be advantageous for precursors of the shaped porous bodies to comprise a material that is not only compositionally pure, but also phase pure, or capable of being converted to phase pure material with appropriate processing. As used herein, the phrase "compositionally pure" is meant to indicate a material that is substantially a single substance, with only trace impurities being present. On the other hand, the phrase "phase pure" is meant to indicate a homogeneity in the phase of the material. For example, if precursors of the shaped porous bodies comprise transition alumina precursors, or transition aluminas, that are converted to alpha-alumina during processing to provide the shaped porous bodies, a high phase purity would indicate that the transition aluminas had been converted so that the shaped porous body comprises at least about 90%, or at least 95%, or even about 99% alpha-alumina phase purity (i.e., alpha-alumina). In those applications where such a phase purity is desired, precursors of the shaped porous bodies may desirably comprise one or more transition alumina precursors or transition aluminas.

Precursors of the shaped porous bodies upon which the present catalysts are desirably based may, if desired, comprise a blend of one or more precursor aluminas. If desired, such a blend may not only comprise at least two precursor aluminas, but may also comprise two secondary particle sizes of the same precursor alumina. As used herein, the phrase "precursor aluminas" is meant to include transition alumina precursors, transition aluminas, and other alpha-alumina precursors. Further, as used herein, the phrase "secondary particle" means an aggregate of primary particles of a precursor alumina. Primary particles of precursor aluminas are individual crystallites of the precursor aluminas and are typically on the order of nanometers in size and as such, are typically most accurately measured by x-ray diffraction. Secondary particles are aggregates of at least two of these primary particles, have sizes on the order of micrometers, and may be most accurately measured by light-scattering or sedimentation methods.

If the use of such a blend is desired, any ratio of the selected precursor aluminas may be used. The selected precursor aluminas may be provided in substantially equal amounts, or, a majority of one may be provided. Exemplary ratios for blends comprising two precursor aluminas, or two secondary particle sizes of one precursor alumina, may thus range from 1:1, to as much as 100:1. Typically, ranges of from 1:1 to 10:1, or from 1:1 to 5:1 may be employed. If these are blends of two particle sizes, it may be preferable that the larger of the two particle sizes is present in the majority. More than two precursor aluminas may also be blended, and in these embodiments as well, the selected aluminas, or particle sizes, may be present in relatively equal amounts, one or more are in a majority, one or more are in the minority, etc. Thus, suitable ratios for these blends may be from about 1:1:1 (or 1:1:1:1, etc.) to about 100:1:1 (or 100:1:1:1, etc) or from about 1:1:1 to about 10:1:1 (or 10:1:1:1, etc.), or from about 1:1:1 to about 5:1:1 (or 5:1:1:1, etc).

In those embodiments of the invention wherein precursors of the shaped porous bodies comprise one or more transition alumina precursors, transition aluminas, or other alpha-alumina precursors, the porous body precursors and/or shaped porous bodies may desirably be fluoride affected, as may be achieved by incorporating therein or exposing the porous body precursors and/or shaped porous bodies to fluorine-containing species, as may be provided in gaseous form, in gaseous or liquid solution, or via the provision of solid fluorine-containing source operatively disposed relative to the porous body precursors and/or shaped porous bodies. For advantages provided in processing, any such fluoride effect may desirably be achieved via exposure of the porous body precursors and/or shaped porous bodies to one or more fluorine-containing species in gaseous form or in gaseous solution. The particulars of such gaseous fluoride affectation are described in copending, commonly assigned PCT application no. PCT/US2006/016437, the entire disclosure of which is hereby incorporated by reference herein for any and all purposes.

Shaped porous bodies upon which the present catalyst are based may also include modifiers, or be prepared utilizing modifiers that are eliminated during processing, to change the chemical and/or physical properties of the shaped porous bodies or end-use products based upon the shaped porous bodies. If inclusion of the same is desired or required, any chosen modifier(s) can be added during any stage of the process of forming the shaped porous bodies, or at one or more steps in the process. For example, a metal oxide modifier can be added to the shaped porous body raw materials prior to, or after, a mixing/mulling step, prior to, or after, formation of the shaped porous body precursors, or before or after drying, or other thermal processing of the shaped porous bodies.

As used herein, "modifier" means a component added to a shaped porous body to introduce desirable properties such as improved end-use performance. More particularly, modifiers can be inorganic compounds or naturally occurring minerals which may be added in order to, e.g., impart certain physical properties or surface chemical properties to the shaped porous bodies and/or end-use products based thereupon.

Precursors of the shaped porous body precursors may comprise any other components, in any amounts, necessary or desired for processing, such as, e.g., water, acid, dopants, etc., of common knowledge to those of ordinary skill in the art of the production of shaped porous bodies for use as structures or supports. In those embodiments wherein the shaped porous bodies comprise transition alumina precursors or transition aluminas, the shaped porous bodies may comprise precursor catalyst compounds that have elements that may desirably be incorporated onto the surface or into the lattice structure of the alpha-alumina particles. Examples of compounds useful for forming these incorporated catalysts include inorganic and organic compounds that form catalysts such as metals, metal carbides, organo-metallic compounds and metal oxides, such as oxides of cerium, manganese, tin, and rhenium.

The shaped porous body precursors may also comprise other organic compounds e.g., binders and dispersants (such as those described in *Introduction to the Principles of Ceramic Processing*, J. Reed, Wiley Interscience, 1988), or pore formers, to facilitate the shaping, or to alter the porosity, of the shaped porous bodies. Pore formers (also known as burn out agents) are materials used to form specially sized pores in the shaped porous bodies by being burned out, sublimed, or volatilized. Pore formers are generally organic, such as ground walnut shells, granulated polyolefins, such as polyethylene and polypropylene, but examples of inorganic pore formers are known. The pore formers are usually added to the shaped porous body raw materials prior to shaping. During a drying or calcining step or during the conversion of the alpha-alumina precursor to alpha-alumina, the pore formers may typically be burned out, sublimed, or volatilized. In some embodiments of the present catalysts, the pore size distribution and surface area of the shaped porous bodies upon which the catalysts are based may advantageously be provided without the use of such pore formers, thereby eliminating the cost and processing time associated with their use.

Whatever the raw materials selected for use in preparing the shaped porous bodies, they are desirably of sufficient purity so that there are limited undesired reactions between any of them. Any impurities are not present in a quantity sufficient to substantially detrimentally impact the properties of the shaped porous bodies and/or catalysts based thereupon.

In particular, any impurities are desirably limited to not more than 3 wt %, or even not more than 1.5 wt %, of the total weight of the shaped porous bodies.

The shaped porous bodies may be formed according to any suitable known method known to those of ordinary skill in the chemical engineering art. Typically, the desired components of the shaped porous bodies precursors, i.e., at least the desired refractory support materials, are first combined, in any form and any order, by any suitable method known in the art. Examples of suitable techniques for combining the shaped porous body materials include ball milling, mix-mulling, ribbon blending, vertical screw mixing, V-blending, and attrition milling. The mixture may be prepared dry (i.e., in the absence of a liquid medium) or wet.

Once mixed, the shaped porous body materials may be formed by any suitable method, such as e.g., injection molding, extrusion, isostatic pressing, slip casting, roll compaction and tape casting. Each of these is described in more detail in *Introduction to the Principles of Ceramic Processing*, J. Reed, Chapters 20 and 21, Wiley Interscience, 1988, incorporated herein by reference in its entirety for any and all purposes. Suitable shapes for the shaped porous bodies generally can include without limitation pills, chunks, tablets, pieces, spheres, pellets, tubes, wagon wheels, toroids having star shaped inner and outer surfaces, cylinders, hollow cylinders, amphora, rings, Raschig rings, honeycombs, monoliths, saddles, cross-partitioned hollow cylinders (e.g., having at least one partition extending between walls), cylinders having gas channels from side wall to side wall, cylinders having two or more gas channels, and ribbed or finned structures. If cylinders, the porous body precursors may be circular, oval, hexagonal, quadrilateral, or trilateral in cross-section. In those embodiments of the invention wherein the shaped porous bodies are intended for end use as catalysts, the shaped porous bodies may desirably be formed into a rounded shape, e.g., pellets, rings, tablets and the like, having diameters of from about 0.1 inch (0.25 cm) to about 0.8 inch (2 cm).

Precursors of the shaped porous body so formed may then optionally be heated under an atmosphere sufficient to remove water, decompose any organic additives, or otherwise modify the precursors prior to introduction into a kiln, oven, pressure-controlled reaction vessel or other container for any further treatment required for processing into shaped porous bodies. Suitable atmospheres include, but are not limited to, air, nitrogen, argon, hydrogen, carbon dioxide, water vapor, those comprising fluorine-containing gases or combinations thereof.

In some embodiments, the shaped porous bodies may desirably be washed to remove any soluble residues thereon prior to the deposition of the components of the end-use product based thereupon. There is some indication that washed shaped porous bodies may exhibit at least marginally enhanced performance, although unwashed shaped porous bodies are also often successfully used in end-use products. If washing is desired, the shaped porous bodies may be washed with hot, e.g., from about 80° C. to about 100° C., demineralized water until the electrical conductivity of the effluent water does not decrease.

At least because of their advantageous pore size distribution, the shaped porous bodies provided by the invention are particularly well suited for use in the manufacture of catalysts based upon the same. More particularly, because the shaped porous bodies have a pore size distribution wherein the percentage of total pore volume present in pores having diameters of less than one micron is minimized, i.e., is less than 25% of the total pore volume, or even less than 20% of the total pore volume, or even less than 15% of the total pore volume, it is expected that catalysts based upon the shaped porous bodies will exhibit a lower diffusional resistance than that exhibited by catalysts based upon shaped porous bodies having a greater percentage of total pore volume being present in pores having diameters of less than one micron. Such lower diffusional resistance, in turn, could result in the present catalyst having higher activity and/or efficiency than catalyst based upon shaped porous bodies having a greater percentage of total pore volume in pores having diameters of less than one micron. Surprisingly, and although this conventional pore size distribution, i.e., a greater percentage of total pore volume in pores having diameters of less than one micron, was thought critical to providing acceptable surface areas for catalytic applications, the shaped porous bodies upon which the present catalyst are based yet exhibit surface areas of at least about the same as these conventional shaped porous bodies, e.g., of at least about 1 $m^2/g$, and in some embodiments even greater, e.g., of at least about 1.15 $m^2/g$ or preferably at least about 1.3 $m^2/g$, or even greater.

The present catalysts are expected to be useful in many applications, and particularly useful for the epoxidation of alkenes, partial oxidation of methanol to formaldehyde, partial selective oxidation of saturated hydrocarbons to olefins, selective hydroformylation of olefins, selective hydrogenations, selective hydrogenation of acetylenes in cracked hydrocarbon streams, selective hydrogenation of di-olefins in olefin-di-olefin-aromatic streams also known as pyrolysis gasoline, and selective reduction of $NO_x$ to $N_2$. Other catalytic applications for the shaped porous bodies include as carriers for automotive exhaust catalysts for emissions control and as carriers for enzymatic catalysis.

Due to the numerous advantages imparted by the shaped porous bodies to this particular end use, in one embodiment of the invention, the shaped porous body is used as the basis of a catalyst and such catalysts, as well as the processes for making them, are provided. Typically, such processes include at least depositing one or more catalytic species on the shaped porous bodies. Once deposited, the catalytic species can be bound directly on the surface of the shaped porous bodies of the invention, or, the catalytic species may be bound to a washcoat, i.e., another surface which has been applied to the surface of the shaped porous bodies. The catalytic species may also be covalently attached to a macromolecular species, such as synthetic polymer or a biopolymer such as a protein or nucleic acid polymers, which in turn, is bound either directly to the surface of the shaped porous bodies or a washcoat applied thereto. Further, a deposited catalytic species may reside on the surface of the shaped porous bodies, be incorporated into a lattice provided on the surface of the shaped porous bodies, or be in the form of discrete particles otherwise interspersed among the shaped porous bodies.

Non-limiting examples of catalytic species that may advantageously be supported by the shaped porous bodies include metals, solid state compounds, molecular catalysts, enzymes and combinations of these. Metals capable of exhibiting catalytic activity include noble metals, e.g. gold, platinum, rhodium, palladium, ruthenium, rhenium, and silver; base metals such as copper, chromium, iron, cobalt, nickel, zinc, manganese, vanadium, titanium, scandium, and combinations of these. Solid state compounds suitable for use as catalytic species include, but are not limited to, oxides, nitrides and carbides, and one particular example of a class of solid state compounds useful as a catalytic species are the perovskite-type catalysts that comprise a metal oxide composition, such as those described by Golden, U.S. Pat. No. 5,939,354, incorporated herein by reference. Exemplary molecular catalytic species include at least metal Schiff base complexes, metal phosphine complexes and diazaphosphacycles. Non-limiting examples of enzymes useful as catalytic species include lipases, lactases, dehalogenases or combinations of these, with preferred enzymes being lipases, lactases or combinations thereof. Typically, metals are utilized as the catalytic species in catalysts contemplated for use in epoxidation processes, and silver in particular, is preferred.

The desired catalytic species may be deposited on the shaped porous bodies according to any suitable method, to provide catalysts according to the invention. Typically, metal catalytic species are conveniently applied by solution impregnation, physical vapor deposition, chemical vapor deposition or other techniques. Silver is typically deposited on shaped porous bodies to form epoxidation catalysts via solution impregnation and the same is contemplated here.

Typically, the shaped porous bodies will be impregnated one or more times with silver compound solutions sufficient to allow the silver to be provided on the shaped porous bodies in an amount greater than about 5 percent, greater than about 10 percent, greater than about 15 percent, greater than about 20 percent, greater than about 25 percent, preferably, greater than about 27 percent, and more preferably, greater than about 30 percent by weight, based on the weight of the catalyst. Although the amount of silver utilized is not particularly limited, the amount of silver provided in connection with the shaped porous bodies may usually be less than about 70 percent, and more preferably, less than about 50 percent by weight, based on the weight of the catalysts.

In terms of density, the amount of catalytic species, e.g., silver, relative to the surface area of the shaped porous bodies may be about $0.07$ $g/m^2$, or up to about $0.12$ $g/m^2$, or up to about $0.15$ $g/m^2$, or up to about $0.20$ $g/m^2$, or up to about $0.40$ $g/m^2$, or even up to about $0.50$ $g/m^2$, or even $0.65$ $g/m^2$.

Although silver particle size in the finished catalysts is important, the range is not narrow. A suitable silver particle size can be in the range of from about 10 angstroms to about 10,000 angstroms in diameter. A preferred silver particle size ranges from greater than about 100 angstroms to less than about 5,000 angstroms in diameter. It is desirable that the silver be relatively uniformly dispersed within, throughout, and/or on the shaped porous body.

Catalysts according to the present invention desirably comprise rhenium, and may, in certain embodiments, further include one or more additional promoters, such as, e.g., cesium. Rhenium promoted supported silver containing catalysts are known from U.S. Pat. No. 4,761,394 and U.S. Pat. No. 4,766,105, which are incorporated herein by reference. Broadly, the catalysts comprise silver, rhenium or compound thereof, and in some embodiments, a co-promoter such as a further metal or compound thereof and optionally an additional co-promoter such as one or more of sulfur, phosphorus, boron, and compounds thereof, on the support material.

As is known to those skilled in the art, there are a variety of known promoters, or materials which, when present in combination with particular catalytic materials, e.g., silver, benefit one or more aspects of catalyst performance or otherwise act to promote the catalyst's ability to make a desired product, e.g., ethylene oxide or propylene oxide. More specifically, and while such promoters in themselves are generally not considered catalytic materials, they typically may contribute to one or more beneficial effects of the catalysts' performance, for example enhancing the rate, or amount, of production of the desired product, reducing the temperature required to achieve a suitable rate of reaction, reducing the rates or amounts of undesired reactions, etc. Furthermore, and as those of ordinary skill in the art are aware, a material which can act as a promoter of a desired reaction can be an inhibitor of another reaction. For purposes of the present invention, a promoter is a material which has an effect on the overall reaction that is favorable to the efficient production of the desired product, whether or not it may also inhibit any competing reactions that may simultaneously occur.

Known promoters for silver-based, epoxidation catalysts, in addition to rhenium, include, but are not limited to, molybdenum, tungsten, lithium, sodium, manganese, rubidium, and cesium. Rhenium, molybdenum or tungsten may suitably be provided as oxyanions, for example, as perrhenate, molybdate, or tungstate, in salt or acid form. Examples of promoters, their characteristics, and methods for incorporating the promoters as part of the catalyst are described in Thorsteinson et al., U.S. Pat. No. 5,187,140, particularly at columns 11 through 15, Liu, et al., U.S. Pat. No. 6,511,938, Chou et al., U.S. Pat. No. 5,504,053, Soo, et al., U.S. Pat. No. 5,102,848, Bhasin, et al., U.S. Pat. Nos. 4,916,243, 4,908,343, and 5,059,481, and Lauritzen, U.S. Pat. Nos. 4,761,394, 4,766,105, 4,808,738, 4,820,675, and 4,833,261, all incorporated herein by reference in their entirety for any and all purposes.

Catalysts comprising silver as a catalytic species as well as at least rhenium as a promoter are expected to find particular benefit when the present inventive shaped porous bodies are used as the bases thereof. The rhenium component can be provided in various forms, for example, as the metal, as a covalent compound, as a cation or as an anion. The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides and the acids of rhenium. However, the alkali metal perrhenates, ammonium perrhenate, alkaline earth metal perrhenates, silver perrhenates, other perrhenates and rhenium heptoxide may also be used. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, that is, $ReO_4$. Similar chemistries can be exhibited by other metals such as molybdenum and tungsten.

In some embodiments, catalysts comprising silver and rhenium, may additionally comprise a promoting amount of at least one further metal, a promoting amount of rhenium, and optionally a co-promoter. More specifically the further metal is selected from the group of Group IA metals, Group IIA metals, molybdenum, tungsten, chromium, titanium, hafnium, zirconium, vanadium, thallium, thorium, tantalum, niobium, gallium and germanium and mixtures thereof. Preferably the further metal is selected from the Group IA metals such as lithium, potassium, rubidium, sodium and cesium and/or from the Group IIA metals such as calcium and barium. More preferably it is lithium, sodium and/or cesium. Most preferably, it is cesium. Where possible, rhenium, the further metal or the co-promoter is provided as an oxyanion, in salt or acid form. Optional co-promoters include, but are not limited to, tungsten, manganese, molybdenum, chromium, sulfur, phosphorous, boron, and mixtures thereof.

The supported silver catalyst can comprise a rhenium promoter, a first co-promoter, and a second co-promoter; where the quantity of the rhenium promoter deposited on the carrier is greater than 1 mmole/kg, relative to the weight of the catalyst; where the first co-promoter is selected from sulfur, phosphorus, boron, and mixtures thereof; where the second co-promoter is selected from tungsten, molybdenum, chromium, sodium and mixtures thereof; and the total quantity of the first co-promoter and the second co-promoter deposited on the carrier is at most 3.8 mmole/kg, relative to the weight of the catalyst.

The catalyst can comprise a shaped porous body and, deposited on the shaped porous body, silver, a rhenium promoter, a first co-promoter, and a second co-promoter; wherein the molar ratio of the first co-promoter to the second co-promoter is greater than 1, wherein the first co-promoter is selected from sulfur, phosphorus, boron, and mixtures thereof; and wherein the second co-promoter is selected from tungsten, molybdenum, chromium, and mixtures thereof. The catalyst can comprise silver, a rhenium promoter, a first co-promoter, and a second co-promoter on a carrier; wherein the molar ratio of the first co-promoter to the second co-promoter is greater than 1; wherein the first co-promoter is selected from sulfur, phosphorus, boron, and mixtures thereof; and the second co-promoter is selected from tungsten, molybdenum, chromium, sodium and mixtures thereof.

The rhenium and any other desired promoters included in the catalyst are desirably provided in a promoting amount, and such amounts are readily determined by those of ordinary skill in the art. A "promoting amount" of a certain promoter refers to an amount of that promoter that works effectively to provide an improvement in one or more of the properties of a catalyst comprising the promoter relative to a catalyst not comprising said promoter. Examples of catalytic properties include, inter alia, operability (resistance to run-away), selectivity, activity, conversion, stability and yield. The promoting effect provided by the promoters can be affected by a number of variables such as for example, reaction conditions, catalyst preparative techniques, surface area and pore structure and surface chemical properties of the support, the silver and co-promoter content of the catalyst, the presence of other cations and anions present on the catalyst. The presence of other activators, stabilizers, promoters, enhancers or other catalyst improvers can also affect the promoting effects. Generally speaking, promoting amounts of rhenium may be at least about 1 ppmw, at least about 5 ppmw, or between from about 10 ppmw to about 2000 ppmw, often between about 20 ppmw and 1000 ppmw, calculated as the weight of rhenium based on the total weight of the catalyst.

Other promoters and/or co-promoters vary in concentration from about 0.0005 to 1.0 wt. %, preferably from about 0.005 to 0.5 wt. %. For some, e.g., cationic promoters, amounts between about 10 ppm and about 4000 ppm, preferably about 15 ppm and about 3000 ppm, and more preferably between about 20 ppm and about 2500 ppm by weight of cation calculated on the total support material are appropriate. Amounts between about 50 ppm and about 2000 ppm are frequently most preferable. If cesium is used in mixture with other cations, the ratio of cesium to any other cation(s), may vary from about 0.0001:1 to 10,000:1, preferably from about 0.001:1 to 1,000:1.

Methods of preparing epoxidation catalysts are well-known in the art, and any of these are suitable for use in preparing the catalysts to be subjected to the present methods. Generally speaking, the methods involved one or more impregnation steps with one or more solutions comprising the desired catalyst components. Typically, a reduction step is conducted during or after the impregnations, to form metallic silver particles. Thorsteinson et al., U.S. Pat. No. 5,187,140, for example, describes methods of forming catalysts, and is incorporated herein by reference for any and all purposes.

One particular example of an epoxidation of commercial importance is the epoxidation of alkylenes, or mixtures of alkylenes. Many references describe these reactions, representative examples of these being Liu et al., U.S. Pat. No. 6,511,938 and Bhasin, U.S. Pat. No. 5,057,481, as well as the Kirk-Othmer's Encyclopedia of Chemical Technology, 4$^{th}$ Ed. (1994) Volume 9, pages 915-959, all of which are incorporated by reference herein in their entirety for any and all purposes. Although the invention is not so limited, for purposes of simplicity and illustration, catalysts according to the invention useful in epoxidations will be further described in terms of, and with reference to, the epoxidation of ethylene.

Catalysts are a very important factor in the commercial viability of such epoxidation reactions. The performance of catalysts in these reactions is typically evaluated on the basis of the catalysts' selectivity, activity, and stability during the epoxidation reactions. Stability typically refers to how the selectivity or activity of the process changes during the time that a particular batch of catalyst is being used, i.e., as more olefin oxide is produced. Catalysts of the present invention, based upon the shaped porous bodies disclosed herein are expected to provide advantages in selectivity, activity and/or stability resulting from one or more property changes provided by the shaped porous bodies comprising a minimized percentage of the total pore volume being present as pores having diameters of less than 1 micron and a surface area of at least about 1.0 m$^2$/g.

Generally speaking then, the epoxidation reaction may take place in any suitable reactor, for example, fixed bed reactors, continuous stirred tank reactors (CSTR), and fluid bed reactors, a wide variety of which are well known to those skilled in the art and need not be described in detail herein. The desirability of recycling unreacted feed, employing a single-pass system, or using successive reactions to increase ethylene conversion by employing reactors in series arrangement can also be readily determined by those skilled in the art. The particular mode of operation selected is usually dictated by process economics. Conversion of olefin (alkylene), preferably ethylene, to olefin oxide, preferably ethylene oxide, can be carried out, for example, by continuously introducing a feed stream containing alkylene (e.g., ethylene) and oxygen or an oxygen-containing gas to a catalyst-containing reactor at a temperature of from about 200° C. to about 300° C., and a pressure which may vary between about 5 atmospheres (506 kPa) and about 30 atmospheres (3.0 MPa), depending upon the mass velocity and productivity desired. Residence times in large-scale reactors are generally on the order of from about 0.1 seconds to about 5 seconds. Oxygen may be supplied to the reaction in an oxygen-containing stream, such as, air or as commercial oxygen, or as oxygen-enriched air. The resulting alkylene oxide, preferably, ethylene oxide, is separated and recovered from the reaction products using conventional methods.

Any alkylene can be utilized in the process, and examples of those that may desirably be epoxidized include, but are not limited to, 1,9-decadiene, 1,3-butadiene, 2-butene, isobutene, 1-butene, propylene, ethylene, or combinations of these. Preferably, the alkylene comprises ethylene.

Typically, epoxidation reactions may desirably be carried out in the gas phase, with a feed comprising the desired alkylene and oxygen being caused to come in contact with an epoxidation catalyst. Oftentimes, the catalyst is present as a solid material, and more particularly, may be present as a packed bed within the desired reactor. The quantity of catalyst used may be any suitable amount and will depend upon the application. In pilot plant reactors, the quantity of catalyst may be, e.g., less than about 5 kg, while in commercial epoxidation plants, the quantity of catalyst used in the packed bed may be at least about 10 kg, or at least 20 kg, or from about 10$^2$ to 10$^7$ kg or from about 10$^3$ to 10$^6$ kg.

Many epoxidation reactions are carried out as continuous processes, and the same is contemplated here. In such processes, the desired reactor may typically be equipped with heat exchange equipment to control the temperature of the process, within the reactor and/or the catalyst bed.

In one embodiment, the process for the oxidation of an alkylene comprises contacting a reaction mixture feed comprising an alkene, oxygen, and carbon dioxide, with a catalyst comprising a carrier and, deposited on the carrier, silver, a rhenium promoter, a first co-promoter, and a second co-promoter; wherein the carbon dioxide is present in the reactor mixture in a quantity of at most 3 mole percent based on the total reaction mixture; the first co-promoter is selected from sulfur, phosphorus, boron, and mixtures thereof; and the second co-promoter is selected from tungsten, molybdenum, chromium, and mixtures thereof.

The alkylene oxide produced by the present epoxidation process may typically be processed to provide further downstream products, such as, for example, 1,2-diols, 1,2-diol ethers, 1,2-carbonates, and alkanolamines. Since the present invention provides an improved epoxidation method, it is contemplated that the improvements provided will carry forward to provide improvements to these downstream processes and/or products. Improved methods for the production of 1,2-diols, 1,2-diol ethers, 1,2-carbonates, and alkanolamines are thus also provided herein.

The conversion of alkylene oxides into 1,2-diols or 1,2-diol ethers may comprise, for example, reacting the desired alkylene oxide with water, suitably in the presence of an acidic or basic catalyst. For example, for preferential production of the 1,2-diol over the 1,2-diol ether, the alkylene oxide may be reacted with a tenfold molar excess of water, in a liquid phase reaction in the presence of an acid catalyst, e.g., 0.5-1.0 wt % sulfuric acid, based on the total reaction mixture, at 50° C. to about 70° C. at 1 bar absolute, or in a gas phase reaction, at 130° C. to about 240° C. and from about 20 bar to about 40 bar absolute, preferably in the absence of a catalyst. If the proportion of water is lowered, the proportion of the 1,2-diol ethers in the reaction mixture will be increased. The 1-2, diol ethers thus produced may comprise di-ethers, tri-ethers, tetra-ethers or other multi-ethers. Alternative 1,2-diol ethers may be prepared by converting the alkylene oxide with an alcohol, such as methanol or ethanol, or by replacing at least a portion of the water with the alcohol. The resulting 1,2-diols and diol ethers may be utilized in a wide variety of end-use applications in the food, beverage, tobacco, cosmetic, thermoplastic polymer, curable resin system, detergent, heat transfer system, etc., industries.

The conversion of alkylene oxides produced via the method of the present invention into alkanolamines may comprise, for example, reacting the alkylene oxide with ammonia. Anhydrous or aqueous ammonia may be used, although anhydrous ammonia favors the production of monoalkanolamine, and may be used when the same is preferred. The resulting alkanolamines may be used, for example, in the treatment of natural gas. The olefin oxide may be converted into the corresponding 1,2-carbonate by reacting the olefin oxide with carbon dioxide. If desired, a 1,2-diol may be prepared by subsequently reacting the 1,2-carbonate with water or an alcohol to form the 1,2-diol. For applicable methods, reference is made to U.S. Pat. No. 6,080,897, which is incorporated herein by reference.

While only certain features of the invention have been illustrated and described herein, many modifications and changes will occur to those skilled in the art. The following examples further illustrate the invention, without limiting the scope thereof. It is to be understood that the appended claims are intended to cover all such modifications and changes as fall within the true spirit of the invention.

Example 1

Preparation of Shaped Porous Bodies

Two shaped porous body samples were prepared according to the following procedures:

Carrier A (Inventive)

Carrier A is a platelet morphology alpha-alumina shaped porous body according to the present invention. A dry mixture of about 90% a combination of a pseudoboehmite having a higher bulk density and a pseudoboehmite having a lower bulk density and about 10% gamma-alumina powder is prepared and 5.0% formic acid and 4.6% ammonium bifluoride, expressed as percentages by weight of the starting dry mixture are added as aqueous solutions with sufficient water to form an extrudable blend. After mixing, the blend is extruded, dried and fired at temperatures of from about 1000-1400° C. to effect complete conversion of the alumina components to alpha-alumina. The properties of Carrier A are shown in Table 1.

TABLE 1

| Surface area | 1.34 m$^2$/g |
| --- | --- |
| Pore volume | 0.77 mL/g |
| Median pore diameter | 2.0 micron |
| Packing density | 51.9 g/100 cm$^3$ |
| Flat plate crush strength (FPCS) | 9.2 kg |

Carrier B (Comparative)

Carrier B is a platelet morphology alpha alumina shaped porous body incorporating 2 wt % zirconium silicate. A dry mixture of about 78.7% a pseudoboehmite having a higher bulk density, about 19.7% gamma-alumina powder and about 1.6% granular zirconium silicate is prepared and 5.0% formic acid and 4.6% ammonium bifluoride, expressed as percentages by weight of the starting dry mixture are added as aqueous solutions with sufficient water to form an extrudable blend. After mixing, the blend is extruded, dried and fired at temperatures of from about 1000-1400° C. to effect complete conversion of the alumina components to alpha-alumina. The properties of Carrier B are shown in Table 2.

TABLE 2

| Surface area | 1.37 m$^2$/g |
| --- | --- |
| Pore volume | 0.61 mL/g |
| Median pore diameter | 1.6 micron |
| Packing density | 57.4 g/100 cm$^3$ |
| FPCS | 10.9 kg |

Plots of cumulative intrusion (% of total pore volume) vs. pore size (microns) determined by Hg porosimetry for Carriers A and B are shown in FIG. 1. As shown, carrier A has 12% of total pore volume in pores of diameter <1 micron while carrier B has 22% of total pore volume in pores of diameter <1 micron. Further, carrier A has 84.5% of total pore volume in pores having diameters of from about 1 micron to about 5 microns, while carrier B has 74.5% of total pore volume in this range. After adjusting for the total pore volume and packing density, carrier A has 3.8 mL of pore volume in pores of diameter less than 1 micron per 100 cc of the carrier, while carrier B has 7.7 mL of pore volume in pores of diameter less than 1 micron per 100 cc of the carrier. Additionally, carrier A provides 69.5 square meters of surface area per 100 cc of the carrier, while carrier B provides 78.6 square meters of surface area per 100 cc of the carrier.

Example 2

Preparation of Catalysts Based Upon the Shaped Porous Bodies of Example 1

Ethylene epoxidation catalysts having the same target promoter concentrations are prepared based upon carriers A and B according to the following procedures:

Catalyst A-1 (Inventive)

A first impregnation of carrier A (60.39 g) is performed using roughly 140 mL of silver-amine-oxalate solution prepared as described under "Catalyst Preparation" in US 2009/0177000A1 (25.89 wt % Ag), incorporated by reference herein in its entirety for any and all purposes. The carrier is impregnated in an appropriately sized glass vessel which is equipped with stopcocks for impregnating the carrier under vacuum. A separatory funnel which is used for containing the impregnating solution is inserted through a rubber stopper into the top of the impregnating vessel. The impregnating vessel containing the carrier is evacuated to approximately 1-2" (25-50 mm) mercury absolute for 15 minutes, after which the impregnating solution is slowly added to the carrier by opening the stopcock between the separatory funnel and the impregnating vessel. After all the solution empties into the impregnating vessel (about 15 seconds), the vacuum is released and the pressure returned to atmospheric. Following addition of the solution, the carrier remains immersed in the impregnating solution at ambient conditions for 15 minutes, and is thereafter drained of excess solution for 15 minutes.

The silver-impregnated carrier is then roasted as follows to effect reduction of silver on the catalyst surface. The impregnated carrier is spread out in a single layer on stainless steel wire mesh trays then placed on a stainless steel belt (spiral weave) and transported through a 2"×2" (5×5 cm) square heating zone for 2.5 minutes, or equivalent conditions are used for a larger belt operation. The heating zone is maintained at 500° C. by passing hot air upward through the belt and the catalyst particles at the rate of 7.5 standard cubic meters per hour. After being roasted in the heating zone, the catalyst is cooled in the open air to room temperature and weighed.

A second impregnation of the roasted catalyst pills is then performed using a solution prepared by adding 0.5481 g of CsOH solution (0.457 g Cs/g solution), 3.1965 g of ammonium perrhenate solution (0.0381 g Re/g solution), 0.167 g of ammonium sulfate solution (0.279 g $SO_4$/g solution), 0.2671 g of manganous nitrate solution (0.157 g Mn/g solution) and 0.9579 g of diammonium EDTA solution (0.4576 g EDTA/g solution) to 207.6 g of silver-amine-oxalate solution composed of the drained solution from the first impregnation combined with fresh silver-amine-oxalate solution. The impregnation, draining and roasting steps for this second impregnation are carried out analogously to the first impregnation. After draining and roasting, the composition of catalyst A-1 is calculated to be 38.6 wt % Ag, 872 ppm Cs (6.56 µmole Cs/g), 424 ppm Re (2.28 µmole Re/g), 162 ppm $SO_4$ (1.69 µmole $SO_4$/g) and 146 ppm Mn (2.66 µmole Mn/g).

Catalyst B-1 (Comparative)

A first impregnation of carrier B (60.96 g) is performed using roughly 140 mL of silver-amine-oxalate solution prepared as described under "Catalyst Preparation" in US 2009/0177000A1 (25.89 wt % Ag), incorporated by reference herein in its entirety for any and all purposes. The carrier is impregnated in an appropriately sized glass vessel which is equipped with stopcocks for impregnating the carrier under vacuum. A separatory funnel which is used for containing the impregnating solution is inserted through a rubber stopper into the top of the impregnating vessel. The impregnating vessel containing the carrier is evacuated to approximately 1-2" (25-50 mm) mercury absolute for 15 minutes, after which the impregnating solution is slowly added to the carrier by opening the stopcock between the separatory funnel and the impregnating vessel. After all the solution empties into the impregnating vessel (about 15 seconds), the vacuum is released and the pressure returned to atmospheric. Following addition of the solution, the carrier remains immersed in the impregnating solution at ambient conditions for 15 minutes, and is thereafter drained of excess solution for 15 minutes.

The silver-impregnated carrier is then roasted as follows to effect reduction of silver on the catalyst surface. The impregnated carrier is spread out in a single layer on stainless steel wire mesh trays then placed on a stainless steel belt (spiral weave) and transported through a 2"×2" (5×5 cm) square heating zone for 2.5 minutes, or equivalent conditions are used for a larger belt operation. The heating zone is maintained at 500° C. by passing hot air upward through the belt and the catalyst particles at the rate of 7.53 standard cubic meters per hour. After being roasted in the heating zone, the catalyst is cooled in the open air to room temperature and weighed.

A second impregnation of the roasted catalyst pills is then performed using a solution prepared by adding 0.6220 g of CsOH solution (0.457 g Cs/g solution), 3.6224 g of ammonium perrhenate solution (0.0381 g Re/g solution), 0.1885 g of ammonium sulfate solution (0.279 g $SO_4$/g solution), 0.3020 g of manganous nitrate solution (0.157 g Mn/g solution) and 1.0868 g of diammonium EDTA solution (0.4576 g EDTA/g solution) to 207.6 g of silver-amine-oxalate solution composed of the drained solution from the first impregnation combined with fresh silver-amine-oxalate solution. The impregnation, draining and roasting steps for this second impregnation are carried out analogously to the first impregnation. After draining and roasting, the composition of catalyst B-1 is calculated to be 34.1 wt % Ag, 878 ppm Cs (6.61 µmole Cs/g), 427 ppm Re (2.29 µmole Re/g), 163 ppm $SO_4$ (1.70 µmole $SO_4$/g) and 147 ppm Mn (2.68 µmole Mn/g).

The calculated catalyst formulations are summarized in Table 3. As is shown, all concentrations of all components of catalyst A-1 and catalyst B-1 are substantially identical except that catalyst A-1 has a slightly higher silver content.

TABLE 3

| | Catalyst | |
| --- | --- | --- |
| | A-1 | B-1 |
| Carrier | A | B |
| % Ag | 38.6 | 34.1 |
| ppm Cs | 872 | 878 |
| ppm Re | 424 | 427 |
| ppm $SO_4$ | 162 | 163 |
| ppm Mn | 146 | 147 |

Example 3

Use of Catalysts Prepared in Example 2 in an Epoxidation Reaction

Figure 2:
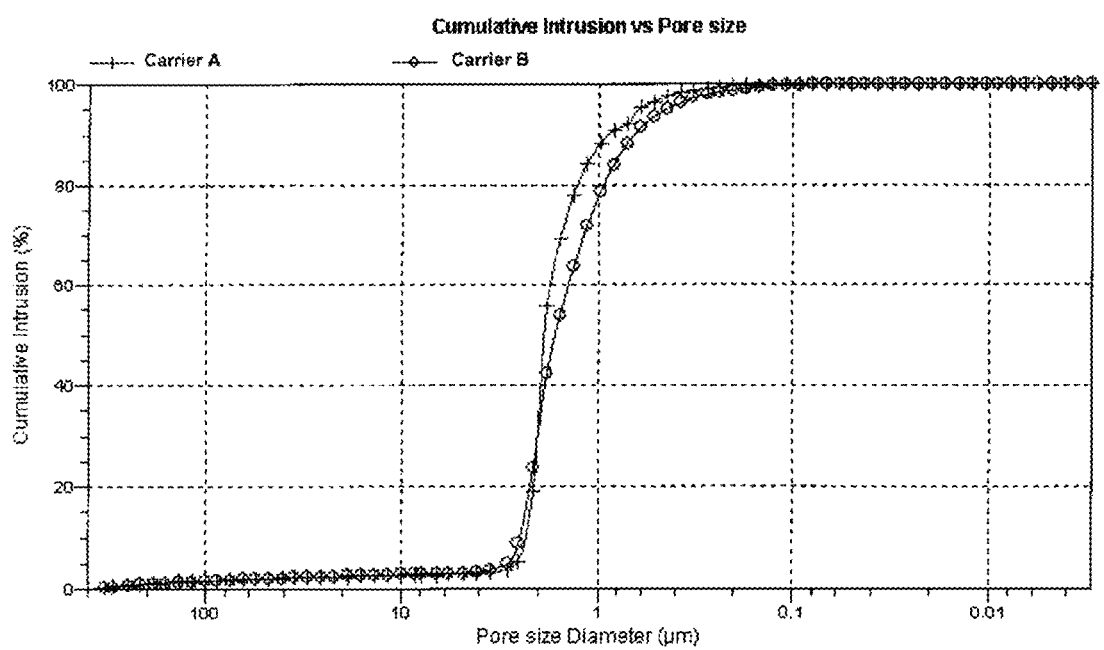
FIG. 2 is a graphical depiction of the cumulative intrusion (% of total pore volume) vs. pore size (microns) determined by mercury porosimetry for shaped porous bodies according to the invention (carrier A) and comparative shaped porous bodies (carrier B)

Catalyst A-1 and catalyst B-1 are tested in standard backmixed autoclaves with gas recycle (similar to well-known, back-mixed, bottom-agitated "Magnedrive" autoclaves described in FIG. 2 of J. M Berty, "Reactor for vapor Phase-Catalytic Studies" *Chemical Engineering Progress*, Vol. 70, No. 5, pages 78-84 (1974)). The feed compositions are: 30 mole-% ethylene, 8 mole-% oxygen, 3.0 mole-% carbon dioxide, 0.5 mole-% ethane and various ppmv levels of ethyl chloride. The volume of each catalyst charge is 0 cm³. Flow rates are about 640 liter/hour. System pressures are about 1900 KPa-gauge. The standard deviation of a single test result reporting catalyst activity in accordance with the procedures described herein is about 1.2° C. The standard deviation, of course, will depend upon the quality of the equipment and precision of the techniques used in conducting the tests, and thus will vary. These standard deviations are believed to apply to the test results reported herein.

Figure 3:
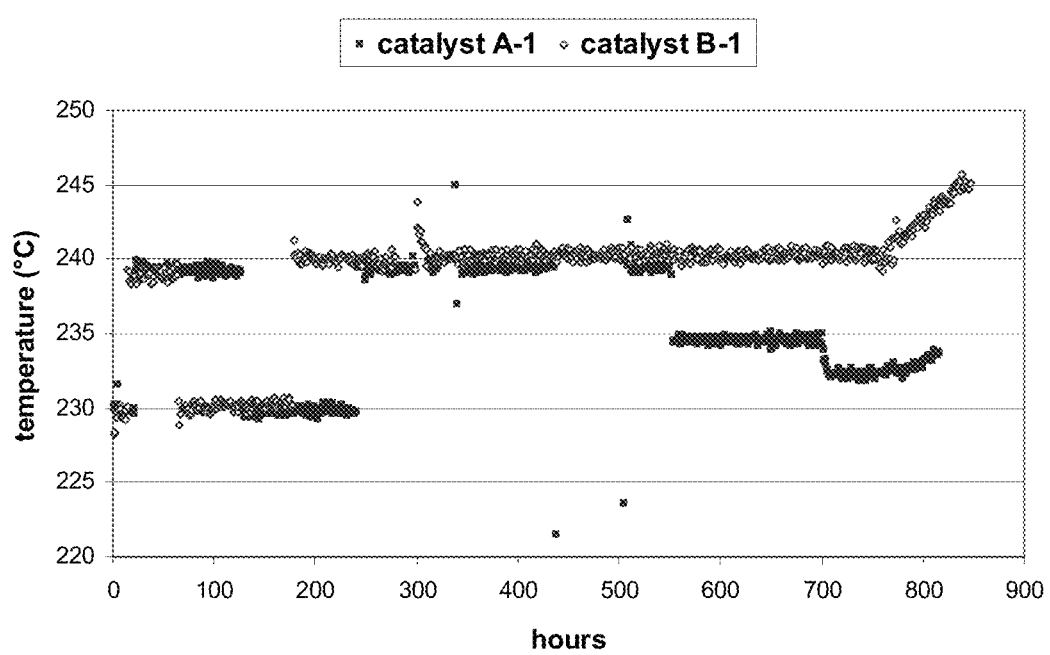
FIG. 3 is a graphical depiction of the temperature history of two ethylene oxide processes utilizing a catalyst according to the present invention (catalyst A-1) and a comparative catalyst (catalyst B-1)
Figure 4:
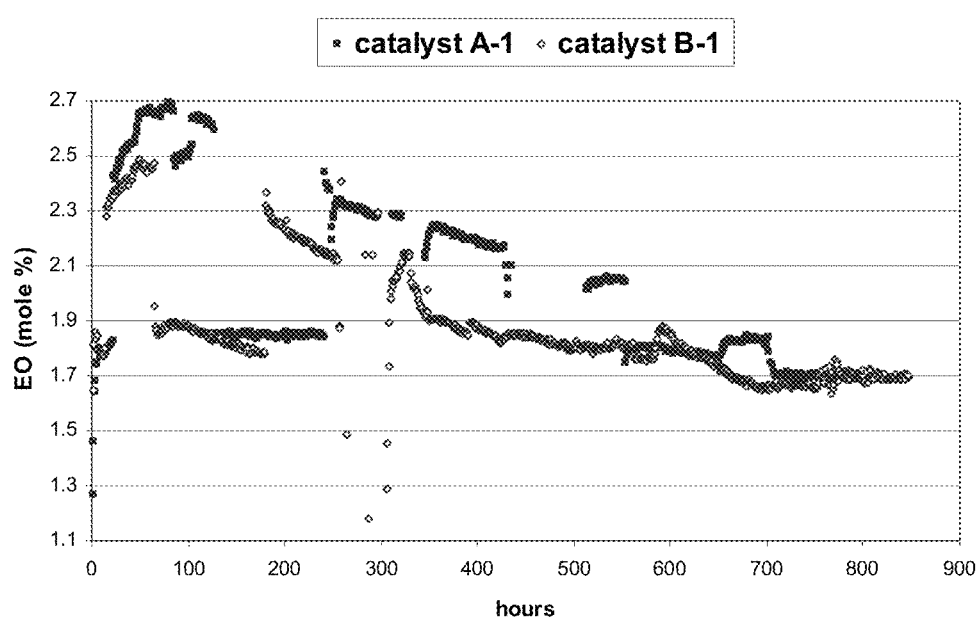
FIG. 4 is a graphical depiction of the ethylene oxide production over time for a catalyst according to the present invention (catalyst A-1) and a comparative catalyst (catalyst B-1)
Figure 5:
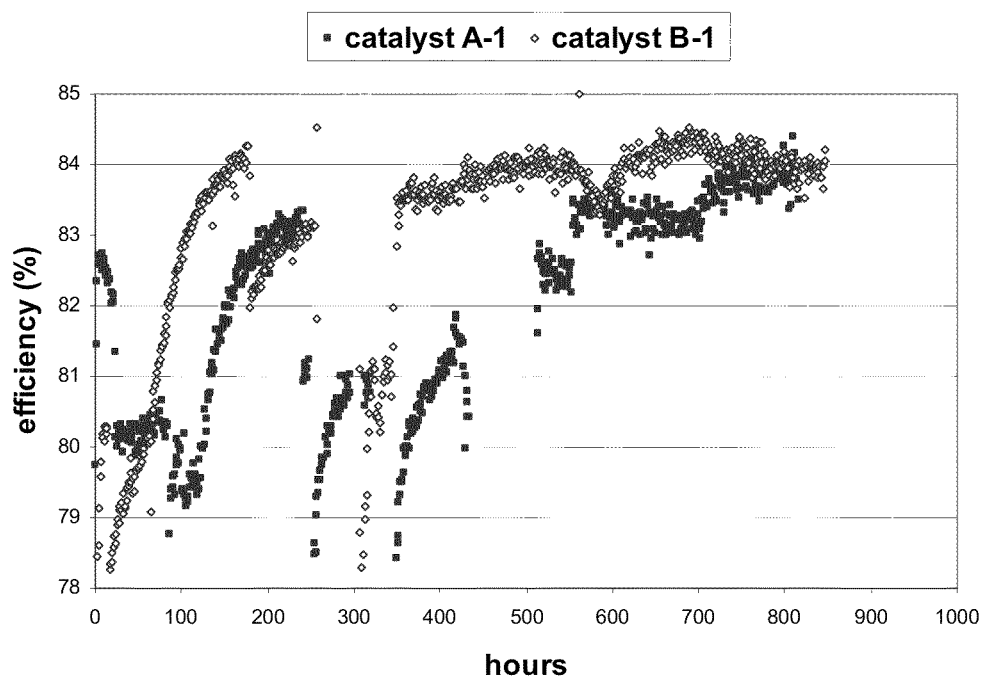
FIG. 5 is a graphical depiction of the efficiency over time for a catalyst according to the present invention (catalyst A-1) and a comparative catalyst (catalyst B-1) when used in a process for the production of ethylene oxide.

Catalyst performances observed are summarized in FIGS. 3, 4 and 5. FIG. 3 shows the operating temperature history of the two runs. Both runs are started at 230° C. The operating temperatures are then raised to 240° C. after about 12 hours. Temperatures and chloride moderator concentrations are varied during the run in order to determine parametric responses of the catalysts to the changes. At the end of the runs, the operating mode is switched from constant temperature operation to constant EO productivity operation controlling at an outlet EO concentration of 1.7 mole-% in order to compare the selectivities and the activities of the catalysts at the same EO productivity. For catalyst A-1 this occurs at about 700 hours and for catalyst B-1 at about 760 hours.

FIGS. 4 and 5 show reactor outlet EO concentrations and selectivities vs. run time. During the first operating mode, when the reactors are operated at constant temperatures, catalyst A-1 gives higher outlet EO concentrations than the corresponding outlet EO from catalyst B-1. To compare catalyst selectivities, in the second mode of operation, the operating temperatures of both reactors are adjusted to produce the same amount of EC). The selectivities of the two runs are about the same at the same EO productivity. However, the operating temperature of catalyst A-1 is about 8° C. lower. This significant reduction cannot be attributed to the minor differences in catalyst composition, and this example thus demonstrates that a catalyst prepared on the carrier having a lower percentage of total pore volume present in pores having a diameter of less than 1 micron gives higher activity without compromising catalyst selectivity.

Example 4

Preparation of Shaped Porous Bodies

Two shaped porous body samples were prepared according to the following procedures:

Carrier C (Inventive)

Carrier C is a platelet morphology alpha-alumina shaped porous body according to the present invention. A dry mixture of about 78.7% a combination of a pseudoboehmite having a higher bulk density and a pseudoboehmite having a lower bulk density, about 19.7% gamma-alumina powder, and about 1.6% granular zirconium silicate is prepared and 5.0% formic acid and 4.6% ammonium bifluoride, expressed as percentages by weight of the starting dry mixture, are added as aqueous solutions with sufficient water to form an extrudable blend. After mixing, the blend is extruded, dried, and fired at temperatures of from about 1000-1400° C. to effect complete conversion of the alumina components to alpha-alumina. The properties of Carrier C are shown in Table 4.

TABLE 4

| Surface area | 1.31 m²/g |
|---|---|
| Pore volume | 0.67 mL/g |
| Median pore diameter | 1.8 micron |
| Packing density | 52.5 g/100 cm³ |
| Flat plate crush strength (FPCS) | 8.8 kg |

Carrier D (Comparative)

Carrier D is a platelet morphology alpha alumina shaped porous body. A dry mixture of about 78.7% a pseudoboehmite having a higher bulk density, about 19.7% gamma-alumina powder, and about 1.6% granular zirconium silicate is prepared and 5.0% formic acid and 4.6% ammonium bifluoride, expressed as percentages by weight of the starting dry mixture, are added as aqueous solutions with sufficient water to form an extrudable blend. After mixing, the blend is extruded, dried, and fired at temperatures of from about 1000-1400° C. to effect complete conversion of the alumina components to alpha-alumina. The properties of Carrier D are shown in Table 5.

TABLE 5

| Surface area | 1.31 m²/g |
|---|---|
| Pore volume | 0.61 mL/g |
| Median pore diameter | 1.9 micron |
| Packing density | 55.4 g/100 cm³ |
| FPCS | 9.3 kg |

Figure 6:
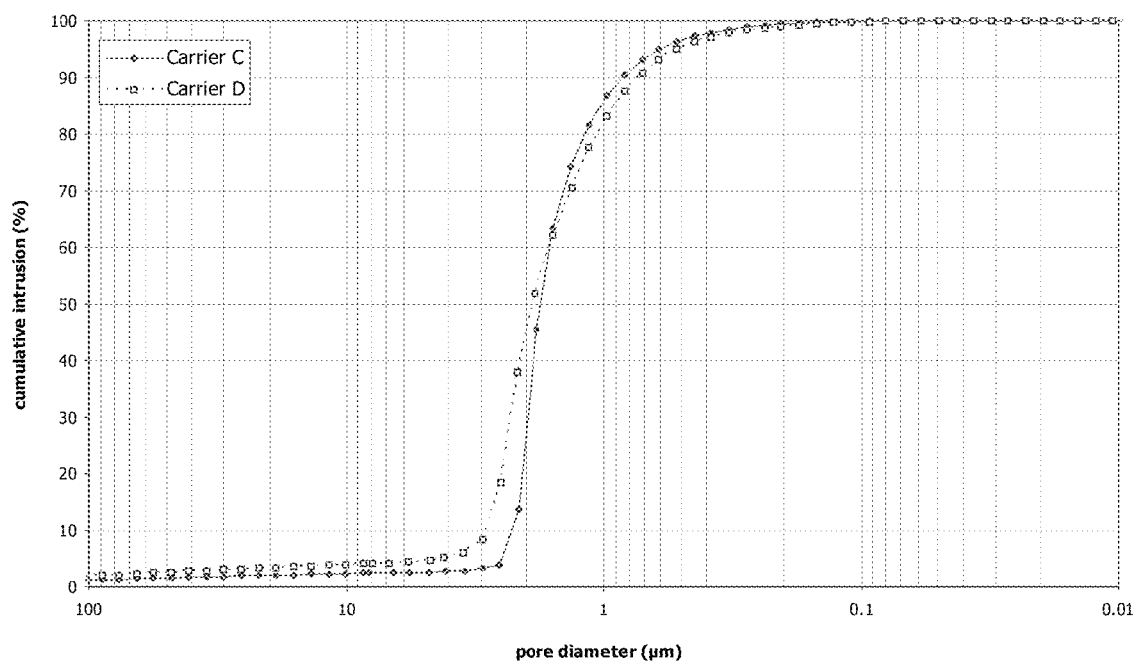
FIG. 6 is a graphical depiction of the cumulative intrusion (% of total pore volume) vs. pore size (microns) determined by mercury porosimetry for shaped porous bodies according to the invention (carrier C) and comparative shaped porous bodies (carrier D)

Plots of cumulative intrusion (% of total pore volume) vs. pore size (microns) determined by Hg porosimetry for Carriers C and D are shown in FIG. 6. As shown, Carrier C has 14% of total pore volume in pores of diameter <1 micron while Carrier D has 18% of total pore volume in pores of diameter <1 micron. Further, carrier C has 83.5% of total pore volume in pores having diameters of from about 1 micron to about 5 microns, while carrier D has 77.7% of total pore volume in this range. After adjusting for the total pore volume and packing density, carrier C has 4.9 mL of pore volume in pores of diameter less than 1 micron per 100 cc of the carrier, while carrier D has 6.1 mL of pore volume in pores of diameter less than 1 micron per 100 cc of the carrier. Additionally, carrier C provides 68.8 square meters of surface area per 100 cc of the carrier while carrier D provides 72.6 square meters of surface area per 100 cc of the carrier.

Example 5

Preparation of Catalysts Based Upon the Shaped Porous Bodies of Example 4

Ethylene epoxidation catalysts having the same target promoter concentrations are prepared based upon carriers C and D according to the following procedures:

Catalyst C-1 (Inventive)

A first impregnation of carrier C (20.45 g) is performed using roughly 50 mL of silver-amine-oxalate solution prepared as described under "Catalyst Preparation" in US 2009/177000 A1 (25.89 wt % Ag), incorporated by reference herein in its entirety for any and all purposes. The carrier is impregnated in an appropriately sized glass vessel which is equipped with stopcocks for impregnating the carrier under vacuum. A separatory funnel which is used for containing the impregnating solution is inserted through a rubber stopper into the top of the impregnating vessel. The impregnating vessel containing the carrier is evacuated to approximately 1-2" mercury absolute for 15 minutes, after which the impregnating solution is slowly added to the carrier by opening the stopcock between the separatory funnel and the impregnating vessel. After all the solution empties into the impregnating vessel (about 15 seconds), the vacuum is released and the pressure returned to atmospheric. Following addition of the solution, the carrier remains immersed in the impregnating solution at ambient conditions for 15 minutes, and is thereafter drained of excess solution for 15 minutes.

The silver-impregnated carrier is then roasted as follows to effect reduction of silver on the catalyst surface. The wet impregnated carrier pills are spread out in a monolayer on a stainless steel wire mesh tray (SS-316 with a 10.5 cm×8 cm square SS mesh with 1 mm apertures welded on the top) and introduced in to a box furnace (Thermolyne—4800 ThermoFischer Make, Barnstead, operating temperature range 100-1200° C.). The tray has a 5' long ⅛" O.D. coiled SS tube welded to one end to feed air into the box tray. The coiled tube is positioned so that it can be routed out of the back of the box furnace through a small port for air supply. The coiled tube can serve as a pre-heater for the air prior to its entry in to the box tray containing impregnated carrier pills. Before introducing the impregnated carrier in to the box furnace, the furnace is preheated to 30° C. higher than the target roasting temperature (300° C.) to offset a drop in temperature when the furnace is opened for introducing the tray. The furnace is switched off prior to opening the door of the furnace to place the tray. The ⅛" SS tube (which is part of the roasting tray) is taken out of the furnace through a port in the rear wall of the furnace and connected to a supply of air (Zero air grade cylinder). This operation typically takes 15 seconds. A pair of tongs is used for transferring the roasting tray in to and out of the furnace. The air flow is adjusted to 50±5 liters per minute. The furnace is switched on and its temperature is reset at 300° C. After being roasted at 300° C. for 10 minutes, the catalyst is taken out from the box furnace, cooled in the open air to room temperature and weighed.

A second impregnation of the roasted catalyst pills is then performed using a solution prepared by adding 0.1982 g of CsOH solution (0.4564 g Cs/g solution), 0.2034 g of lithium acetate solution (0.023 g Li/g solution), 0.0828 g of sodium acetate solution (0.071 g Na/g solution), 1.7645 g of ammonium perrhenate solution (0.0359 g Re/g solution), 0.0809 g of ammonium sulfate solution (0.2789 g $SO_4$/g solution), 0.1214 g of manganous nitrate solution (0.1552 g Mn/g solution) and 0.6463 g of diammonium EDTA solution (0.4128 g EDTA/g solution) to 71.5 g of silver-amine-oxalate solution composed of the drained solution from the first impregnation combined with fresh silver-amine-oxalate solution. The impregnation, draining and roasting steps for this second impregnation are carried out analogously to the first impregnation. After draining and roasting, the composition of catalyst C-1 is calculated to be 33.11 wt % Ag, 769 ppm Cs (5.79 µmole Cs/g), 40 ppm Li (5.76 µmole Li/g), 50 ppm Na (2.17 µmole Na/g), 538 ppm Re (2.89 µmole Re/g), 192 ppm $SO_4$ (2.00 µmole $SO_4$/g) and 160 ppm Mn (2.91 µmole Mn/g).

Catalyst D-1 (Comparative)

A first impregnation of carrier D (20.25 g) is performed using roughly 50 mL of silver-amine-oxalate solution prepared as described under "Catalyst Preparation" in US 2009/177000A1 (25.89 wt % Ag), incorporated by reference herein in its entirety for any and all purposes. The carrier is impregnated in an appropriately sized glass vessel which is equipped with stopcocks for impregnating the carrier under vacuum. A separatory funnel which is used for containing the impregnating solution is inserted through a rubber stopper into the top of the impregnating vessel. The impregnating vessel containing the carrier is evacuated to approximately 1-2" mercury absolute for 15 minutes, after which the impregnating solution is slowly added to the carrier by opening the stopcock between the separatory funnel and the impregnating vessel. After all the solution empties into the impregnating vessel (about 15 seconds), the vacuum is released and the pressure returned to atmospheric. Following addition of the solution, the carrier remains immersed in the impregnating solution at ambient conditions for 15 minutes, and is thereafter drained of excess solution for 15 minutes.

The silver-impregnated carrier is then roasted as follows to effect reduction of silver on the catalyst surface. The wet impregnated carrier pills are spread out in a monolayer on a stainless steel wire mesh tray (SS-316 with a 10.5 cm×8 cm square SS mesh with 1 mm apertures welded on the top) and introduced in to a box furnace (Thermolyne—4800 ThermoFischer Make, Barnstead, operating temperature range 100-1200° C.). The tray has a 5' long ⅛" O.D. coiled SS tube welded to one end to feed air into the box tray. The coiled tube is positioned so that it can be routed out of the back of the box furnace through a small port for air supply. The coiled tube can serve as a pre-heater for the air prior to its entry in to the box tray containing impregnated carrier pills. Before introducing the impregnated carrier in to the box furnace, the furnace is preheated to 30° C. higher than the target roasting temperature (300° C.) to offset a drop in temperature when the furnace is opened for introducing the tray. The furnace is switched off prior to opening the door of the furnace to place the tray. The ⅛" SS tube (which is part of the roasting tray) is taken out of the furnace through a port in the rear wall of the furnace and connected to a supply of air (Zero air grade cylinder). This operation typically takes 15 seconds. A pair of tongs is used for transferring the roasting tray in to and out of the furnace. The air flow is adjusted to 50±5 liters per minute. The furnace is switched on and its temperature is reset at 300° C. After being roasted at 300° C. for 10 minutes, the catalyst is taken out from the box furnace, cooled in the open air to room temperature and weighed.

A second impregnation of the roasted catalyst pills is then performed using a solution prepared by adding 0.1910 g of CsOH solution (0.4564 g Cs/g solution), 0.1963 g of lithium acetate solution (0.023 g Li/g solution), 0.0800 g of sodium acetate solution (0.071 g Na/g solution), 1.7025 g of ammonium perrhenate solution (0.0359 g Re/g solution), 0.0782 g of ammonium sulfate solution (0.2789 g $SO_4$/g solution), 0.1174 g of manganous nitrate solution (0.1552 g Mn/g solution) and 0.6263 g of diammonium EDTA solution (0.4128 g EDTA/g solution) to 72.2 g of silver-amine-oxalate solution composed of the drained solution from the first impregnation combined with fresh silver-amine-oxalate solution. The impregnation, draining and roasting steps for this second impregnation are carried out analogously to the first impregnation. After draining and roasting, the composition of catalyst D-1 is calculated to be 34.05 wt % Ag, 734 ppm Cs (5.52 µmole Cs/g), 38 ppm Li (5.47 µmole Li/g), 48 ppm Na (2.09 µmole Na/g), 515 ppm Re (2.77 µmole Re/g), 184 ppm $SO_4$ (1.92 µmole $SO_4$/g) and 153 ppm Mn (2.78 µmole Mn/g).

The calculated catalyst formulations are summarized in Table 6. As is shown, all concentrations of all components (except silver) of catalyst D-1 are about 4-5% lower than those of catalyst-C1, whereas the silver content in both the catalysts is similar.

TABLE 6

| | Catalyst | |
|---|---|---|
| | C-1 | D-1 |
| Carrier | C | D |
| % Ag | 33.11 | 34.05 |
| ppm Cs | 769 | 734 |
| ppm Li | 40 | 38 |
| ppm Na | 50 | 48 |
| ppm Re | 538 | 515 |
| ppm $SO_4$ | 192 | 184 |
| ppm Mn | 160 | 153 |

Example 6

Use of Catalysts Prepared in Example 5 in an Epoxidation Reaction

Catalyst C-1 and catalyst D-1 are tested in ¼ inch (outer diameter) stainless steel reactor tubes (once-through operation). An amount of 0.7 g of crushed catalysts (30/50 mesh sized) are thoroughly mixed with 1:1 by weight Denstone (inert from Norton Inc, USA) of the same particle size fraction and loaded in the reactor tubes. The feed compositions are: 30 mole-% ethylene, 8 mole-% oxygen, 1.5 mole-% carbon dioxide, 0.7 mole-% ethane and various ppmv levels of ethyl chloride. The total inlet gas flow rate is adjusted to give a gas hourly space velocity of 10000 $h^{-1}$ as calculated for uncrushed catalyst. Reactor pressures are about 1950 KPa-gauge. The standard deviation of a single test result reporting catalyst activity in accordance with the procedures described herein is about 0.33° C.

Figure 7:
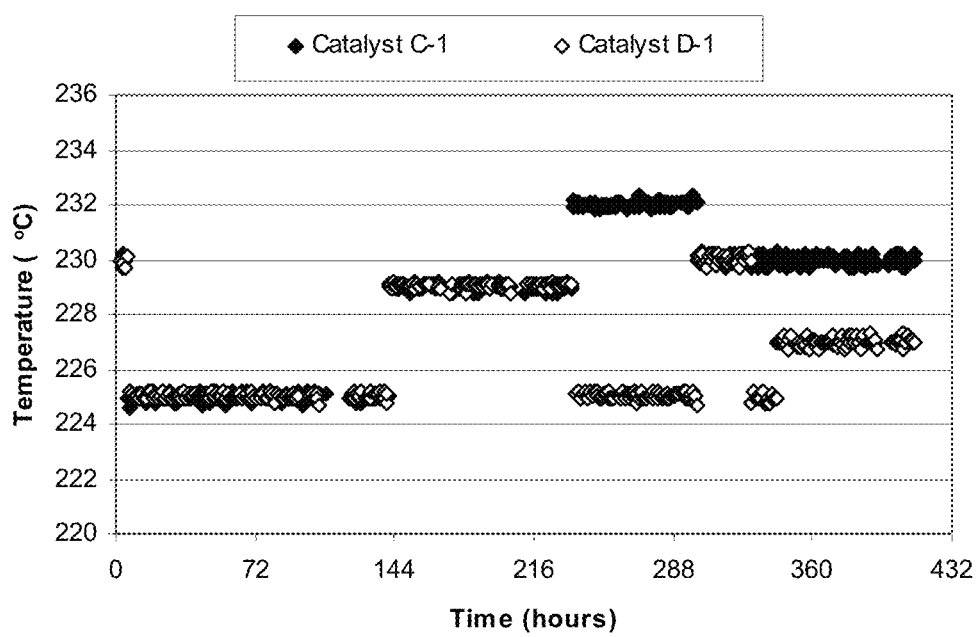
FIG. 7 is a graphical depiction of the temperature history of two ethylene oxide processes utilizing a catalyst according to the present invention (catalyst C-1) and a comparative catalyst (catalyst D-1)
Figure 8:
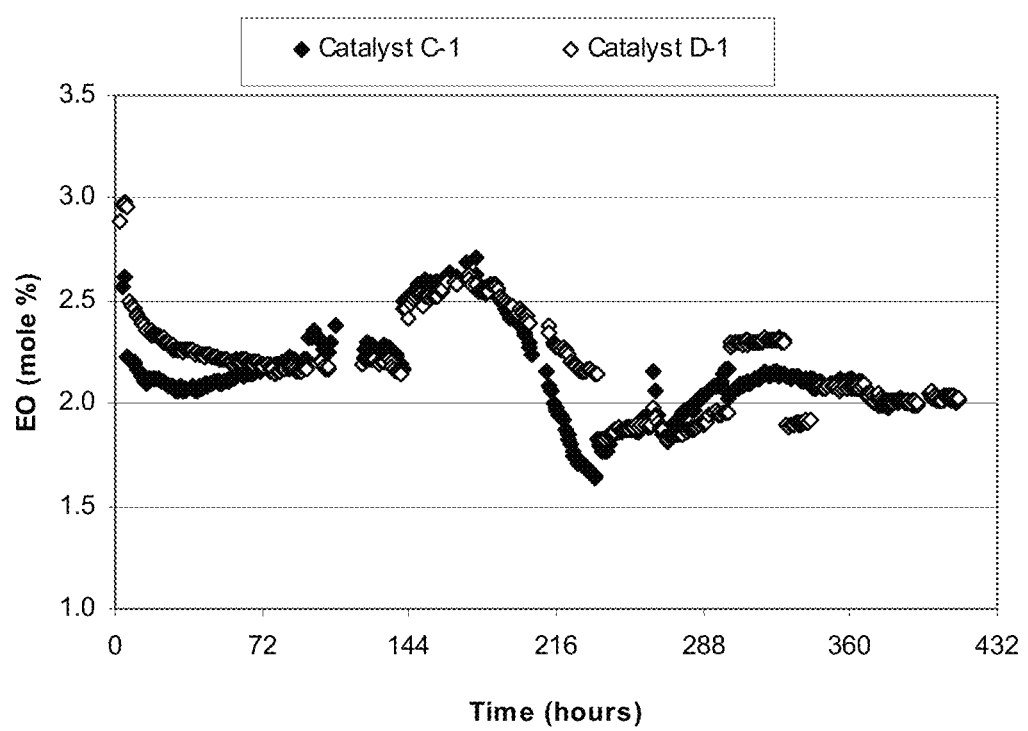
FIG. 8 is a graphical depiction of the ethylene oxide production over time for a catalyst according to the present invention (catalyst C-1) and a comparative catalyst (catalyst D-1)
Figure 9:
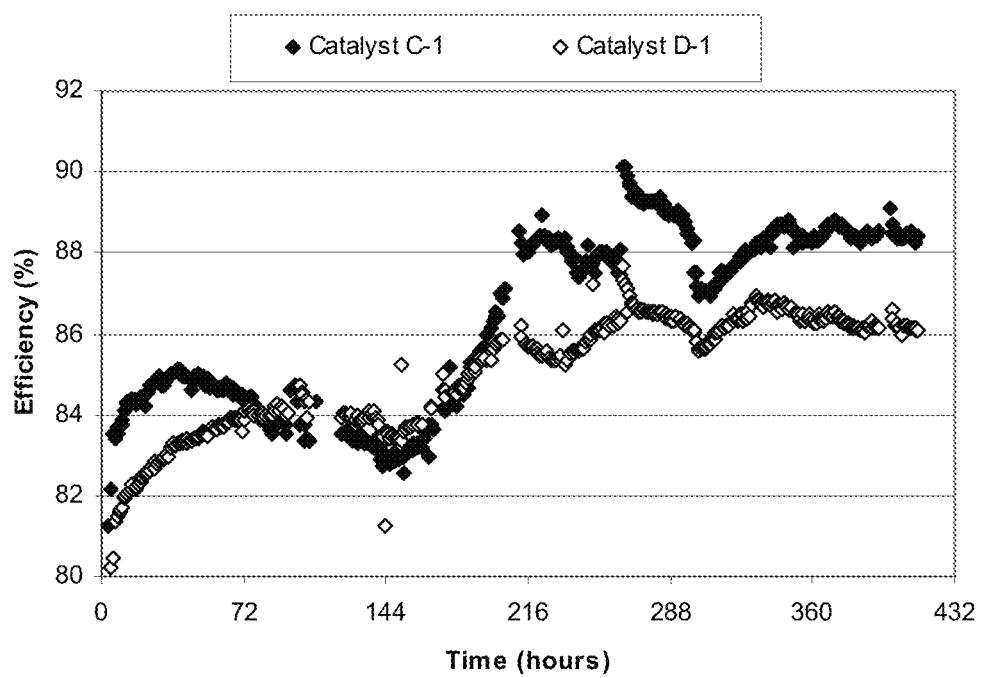
FIG. 9 is a graphical depiction of the efficiency over time for a catalyst according to the present invention (catalyst C-1) and a comparative catalyst (catalyst D-1) when used in a process for the production of ethylene oxide.

Catalyst performances observed are summarized in FIGS. 7, 8 and 9. FIG. 7 shows the operating temperature history of the two runs. Both runs are started at 230° C. The operating temperatures are then reduced to 225° C. after about 7 hours to avoid run away situation due to high outlet EO concentration. Temperatures and chloride moderator concentrations are varied during the run in order to determine parametric responses of the catalysts to the changes. At the end of the runs, the operating mode is switched from constant temperature operation to constant EO productivity operation controlling at an outlet EO concentration of 2.01 mole-% in order to compare the selectivities and the activities of the catalysts at the same EO productivity. This occurs at about 345 h for both the catalysts.

FIGS. 8 and 9 show reactor outlet EO concentrations and selectivities, respectively, vs. run time. During the first operating mode, when the reactors are operated at constant temperatures, catalyst D-1 gives higher outlet EO concentrations than the corresponding outlet EO from catalyst C-1. To compare catalyst selectivities, in the second mode of operation, the operating temperatures of both reactors are adjusted to produce the same amount of EO. The operating temperature of catalyst D-1 is about 3° C. lower than that of catalyst C-1. However, the efficiency of catalyst C-1 is about 2% higher than that of catalyst D-1. This significant improvement in efficiency cannot be attributed to the minor differences in catalyst composition, and this example thus demonstrates that a catalyst prepared on the carrier having a lower percentage of total pore volume present in pores having a diameter of less than 1 micron gives higher selectivity.

We claim:

1. An epoxidation process, comprising reacting, under epoxidation conditions, a feed comprising ethylene and oxygen in the presence of an epoxidation catalyst comprising silver and a promoting amount of rhenium deposited on a shaped porous body, wherein the shaped porous body comprises less than 20% of its total pore volume being present in pores having diameters of less than 1 micron, and a surface area of at least about 1.3 $m^2/g$, wherein the catalyst exhibits a higher activity and/or selectivity when used in the process than a catalyst supported on shaped porous bodies having a greater percentage of their total pore volume in pores having diameters of less than one micron.

2. The process of claim 1, carried out in the gas phase.

3. The process of claim 2, conducted at a temperature of from 200° C. to 300° C.

4. The process of claim 2 or 3, conducted at a pressure of from ambient to 3.0 MPa.

5. The process of claim 1, further comprising converting the ethylene oxide produced into a 1,2-diol, 1,2-diol ether, a 1,2-carbonate, or alkanolamine.

6. The process of claim 5, wherein the conversion comprises reacting the ethylene oxide with water and/or alcohol to produce one or more 1,2-diols or 1,2-diol ethers.

7. The process of claim 6, wherein reaction of ethylene oxide and water is conducted in the presence of an acidic catalyst comprising 0.5 wt. % to 1.0 wt. % sulfuric acid.

8. The process of claim 6 or 7, wherein the process is conducted in the liquid phase at a temperature of from 50° C. to 70° C.

9. The process of claim 6 or 7, wherein the process is conducted in the gas phase at a temperature of from 130° C. to 240° C.

10. The process of claim 5, wherein the conversion comprises reacting the ethylene oxide with ammonia to produce one or more alkanolamines.

11. The process of claim 10, wherein anhydrous ammonia is used and a monoalkanolamine is produced.

12. The process of claim 5, wherein the conversion comprises reacting the ethylene oxide with carbon dioxide to provide a 1,2-carbonate.

* * * * *